United States Patent [19]

Bryant

[11] Patent Number: 5,645,545
[45] Date of Patent: Jul. 8, 1997

[54] SELF REAMING INTRAMEDULLARY NAIL AND METHOD FOR USING THE SAME

[75] Inventor: Mark A. Bryant, Auburn, Ind.

[73] Assignee: Zimmer, Inc., Warsaw, Ind.

[21] Appl. No.: 514,577

[22] Filed: Aug. 14, 1995

[51] Int. Cl.⁶ ........................................ A61B 17/56
[52] U.S. Cl. ........................ 606/62; 606/67; 606/80; 606/79; 606/170; 606/180; 606/96
[58] Field of Search ........................ 606/62, 63, 64, 606/65, 66, 67, 68, 72, 80, 170, 180, 79, 96

[56] References Cited

U.S. PATENT DOCUMENTS

| | | | |
|---|---|---|---|
| 3,554,192 | 1/1971 | Isberner | 128/83 |
| 3,709,218 | 1/1973 | Halloran | 128/92 A |
| 4,016,874 | 4/1977 | Maffei et al. | 128/92 BC |
| 4,135,507 | 1/1979 | Harris | 128/92 BC |
| 4,467,794 | 8/1984 | Maffei et al. | 128/92 BC |
| 4,473,070 | 9/1984 | Matthews et al. | 128/92 E |
| 4,706,659 | 11/1987 | Matthews et al. | 128/92 VD |
| 4,751,922 | 6/1988 | DiPetropolo | 128/92 VJ |
| 4,927,424 | 5/1990 | McConnell et al. | 606/96 |
| 5,034,013 | 7/1991 | Kyle et al. | 606/62 |
| 5,100,404 | 3/1992 | Hayes | 606/62 |
| 5,112,333 | 5/1992 | Fixel | 606/62 |
| 5,122,134 | 6/1992 | Borzone et al. | 606/80 |
| 5,122,141 | 6/1992 | Simpson et al. | 606/62 |
| 5,122,146 | 6/1992 | Chapman et al. | 606/102 |
| 5,268,000 | 12/1993 | Ottieri et al. | 606/62 |

Primary Examiner—Michael Powell Buiz
Assistant Examiner—Mark S. Leonardo
Attorney, Agent, or Firm—Margaret L. Geringer

[57] ABSTRACT

A self-reaming intramedullary nail and method for using the same are disclosed. Nail 10 includes a rotatable reaming head 30 mounted to the distal end 24 of the cannulated nail body 20. A detachable drive shaft 40 connects reaming head 30 through nail body 20 to a conventional rotational drill device 8. Reaming head 30 and drive shaft 40 have longitudinal bores 31, 41 that when connected form a passage for receiving a guide wire 6.

10 Claims, 4 Drawing Sheets

SELF REAMING INTRAMEDULLARY NAIL AND METHOD FOR USING THE SAME

This invention relates to an intramedullary nail and in particular a self-reaming intramedullary nail and a method for using the same with a rotational drive device for reinforcing and stabilizing a bone having a medullary canal.

BACKGROUND OF THE INVENTION

The use of cannulated intramedullary (IM) nails in the internal fixation of fractured long bones is well known in the medical arts. IM nails are inserted in the intramedullary canal of a fractured long bone and fixed across the fracture site to provide increased rigidity of the fracture fragments. Generally, the nails have a longitudinal bore for receiving a guide wire, which is used to assist in the nail insertion. In a conventional nail insertion procedure, the guide wire is inserted into the intramedullary canal from the proximal end of the bone to locate the distal fracture fragment. Thereafter, a series of flexible cannulated reamers are passed in succession over the guide wire to prepare the channel for receiving the IM nail. The IM nail is passed over the guide wire and inserted into the prepared canal. Once the nail is properly inserted, the guide wire is withdrawn and the nail is secured within the fractured bone by locking screws.

SUMMARY OF THE INVENTION

The self-reaming IM nail of this invention eliminates the need for multiple reaming components and nail instruments to prepare the medullary canal for the nail. In addition, the insertion procedure for the nail requires fewer surgical steps, which reduces the length of the surgical procedure. The self-reaming IM nail of this invention includes a rotatable reaming head mounted to the distal end of the cannulated nail body. A detachable drive shaft is used to connect the reaming head through the cannulated nail body to a rotational driver, such as a conventional reaming drill or other suitable device. The reaming head and drive shaft have longitudinal bores that when connected form a passage for receiving a guide wire therethrough.

In a typical insertion procedure, the nail and its attached drive shaft are passed over a guide wire, which has been inserted into the medullary canal of the bone. Next, the rotational driver is connected to the drive shaft, which protrudes from the proximal end of the nail body. With the rotational driver connected to the drive shaft, the nail is positioned against the bone directly in line with the medullary canal. The action of the rotational driver turns the reaming head which clears a passage for the nail as the nail moves down the guide wire. The rotation of the reaming head also draws the nail body into the medullary canal. Once the nail has been inserted to the proper depth within the canal, the rotational driver is disconnected from the drive shaft. Next, the drive shaft is disconnected from the reaming head and withdrawn from the nail body. Finally, the guide wire is withdrawn from the nail and bone and locking screws are inserted to secure the nail within the bone.

Accordingly, an advantage of this invention is to provide for a self-reaming IM nail used to stabilize a bone having a medullary canal.

Another advantage of this invention is to reduces the number of components, instruments and surgical steps required in preparing a medullary canal and inserting an IM nail to stabilize a bone.

Another advantage of this invention is to provide a self-reaming IM nail which includes an elongated and cannulated nail body and a rotatable reaming head and uses a detachable drive shaft for connecting the reaming head through the nail body to a rotational driver, such as a reaming drill.

Other advantages will become apparent upon a reading of the following description.

BRIEF DESCRIPTION OF THE DRAWINGS

A preferred embodiment of the invention has been depicted for illustrative purposes only wherein.

DESCRIPTION OF THE PREFERRED EMBODIMENT

The preferred embodiment herein described is not intended to be exhaustive or to limit the invention to the precise form disclosed. It is chosen and described to explain the principles of the invention and its application and practical use to enable others skilled in the art to utilize its teachings.

Figure 2:
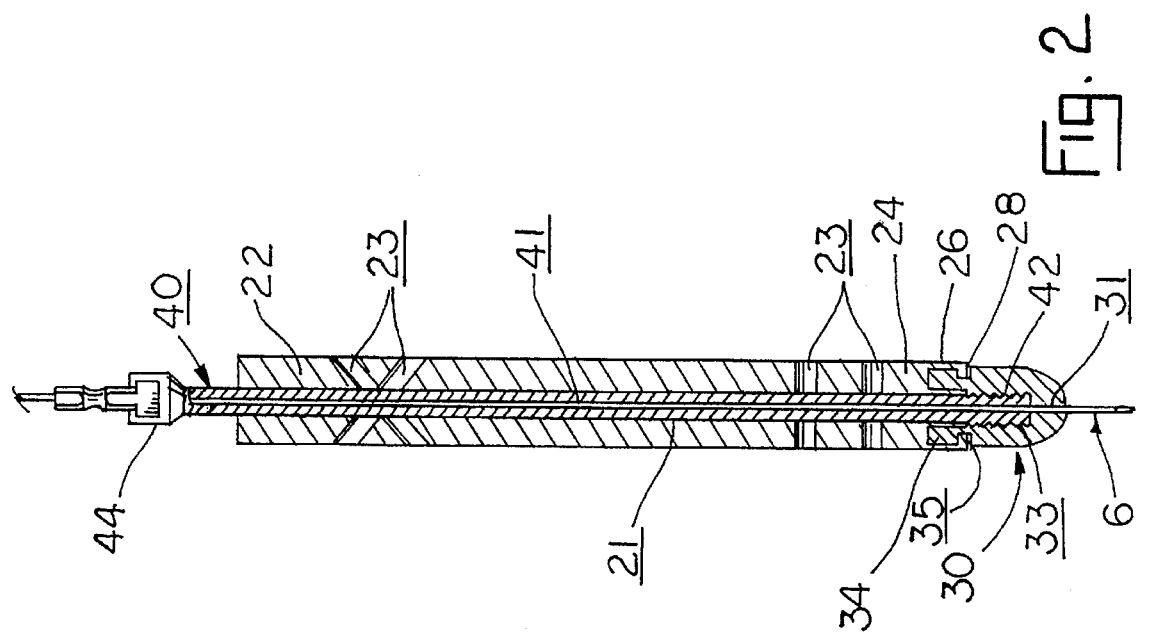
FIG. 2 is a sectional view of the self-reaming IM nail of FIG. 1.
Figure 1:
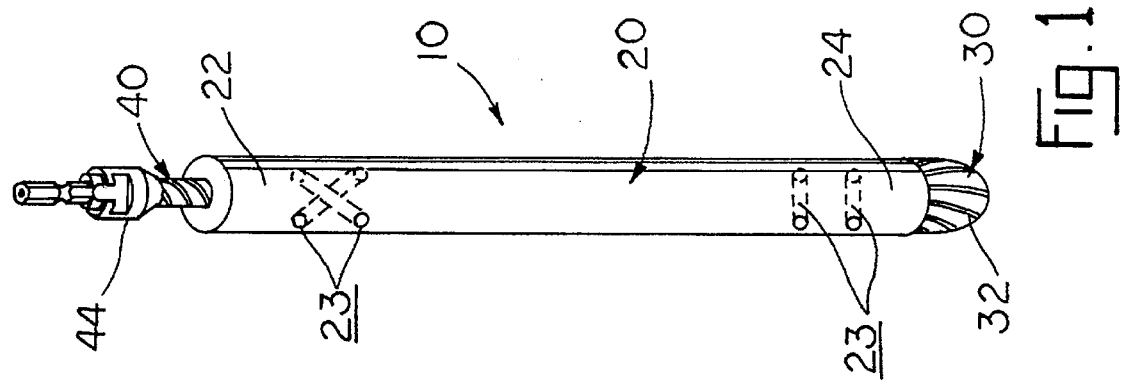
FIG. 1 is a perspective of the self-reaming IM nail assembly of this invention.

FIGS. 1 and 2 show the self-reaming nail 10 and detachable tubular drive shaft 40 of this invention. Nail 10 includes an elongated cannulated body 20 and a rotatable distal reaming head 30. Nail body 20 can be shaped and dimensioned as desired to conform to any suitable intramedullary application. Nail body 20 has a proximal end 22 and distal end 24. As shown in FIG. 2, nail body 20 has a cannulation or longitudinal bore 21 extending between proximal and distal ends 22, 24 for receiving drive shaft 40. Nail distal end 24 includes an annular end flange 26 and an in turned lip 28. Preferably, proximal and distal ends 22, 24 each have a pair of screw bores 23 for receiving locking screws (not shown) as desired. The screw bores 23 may be angled or parallel in orientation to each other as shown respectively in proximal end 22 and distal end 24.

Reaming head 30 includes a plurality of suitable cutting blades 32 and a cylindrical internal neck 34. Neck 34 is journaled within end flange 26 for rotational movement about the longitudinal axis of nail body 20. Neck 34 has an annular recess 35 in which flange lip 28 is seated to secure reaming head 30 to nail body 20. However, other suitable means of attachment of the reamer head 30 to the nail 10 are possible, such as a rotating bearing (not shown), or other suitable attachment mechanisms. Generally, the area prepared or cut by the rotation of reaming head 30 is approximately equal to or slightly greater than the maximum diameter of nail body 20. Reaming head 30 has a longitudinal bore 31 with an enlarged threaded portion 33.

Preferably drive shaft 40 has a flexible tubular body to allow the drive shaft to conform to any curvature of nail bore 21 due to the configuration of nail body 20. The distal end of drive shaft 40 is insertable into the proximal end of nail bore 21 and connectable to reaming head 30. As shown in FIG. 2, the distal end of drive shaft 40 includes threads 42, which are turned into threaded portion 33 of reaming head bore 31; although any suitable connection mechanism can be employed to interconnect or detachably connect the drive shaft to the reaming head within the nail body. When connected to reaming head 30, drive shaft 40 extends beyond the body proximal end 22, as shown in FIG. 2. The proximal end of drive shaft 40 includes a suitable drive end part 44 for connecting the drive shaft to a rotational driver 8, such as a conventional reaming drill (FIGS. 3 and 4) or other suitable device. As shown in FIG. 2, drive shaft 40 has a longitudinal bore 41, which aligns with head bore 31 when connected to the reaming head to form a longitudinal passage for receiving a guide wire 6 therethrough.

Figure 3:
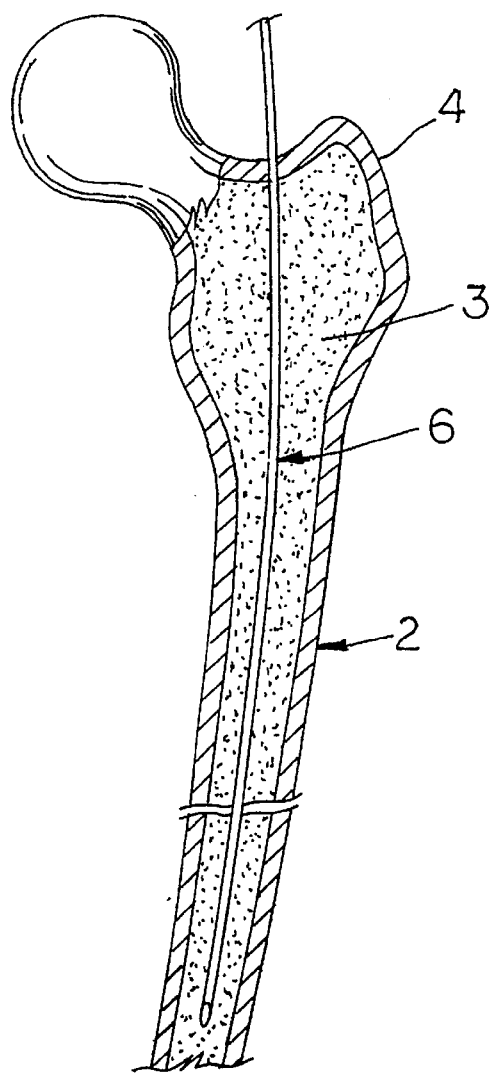
FIG. 3 is a partial sectional view of part of a fractured femur showing a guide wire inserted proximally into the intramedullary channel.
Figure 4:
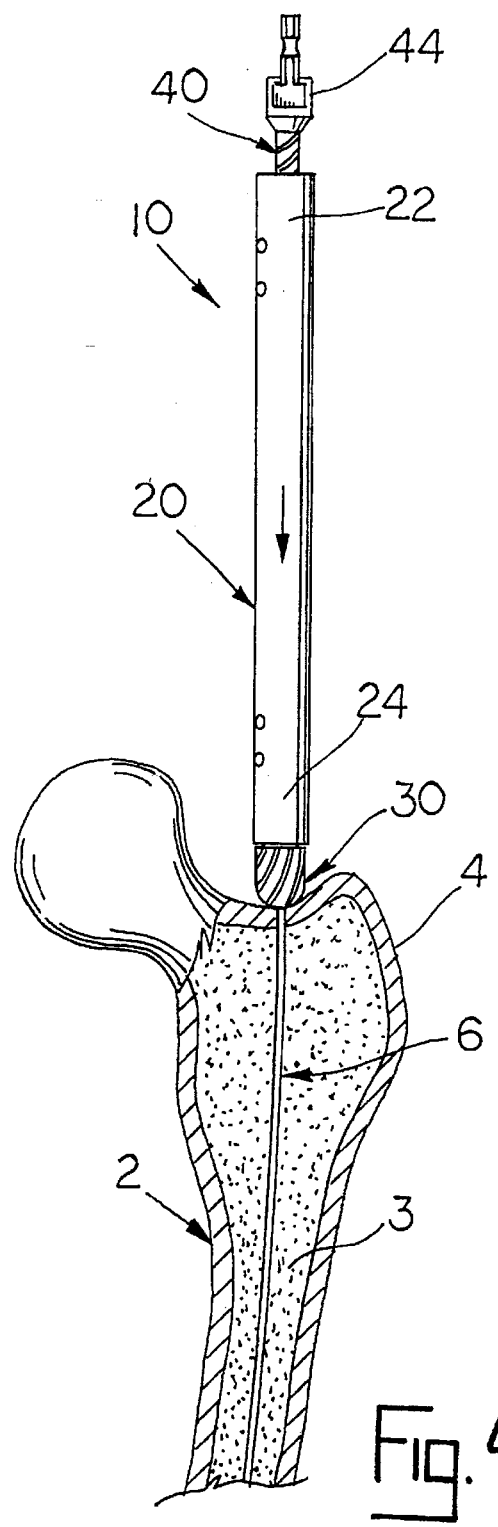
FIG. 4 is a partial sectional view of part of a fractured femur showing the self-reaming IM nail and detachable drive shaft of this invention inserted over the guide wire of FIG. 3.
Figures 5, 6:
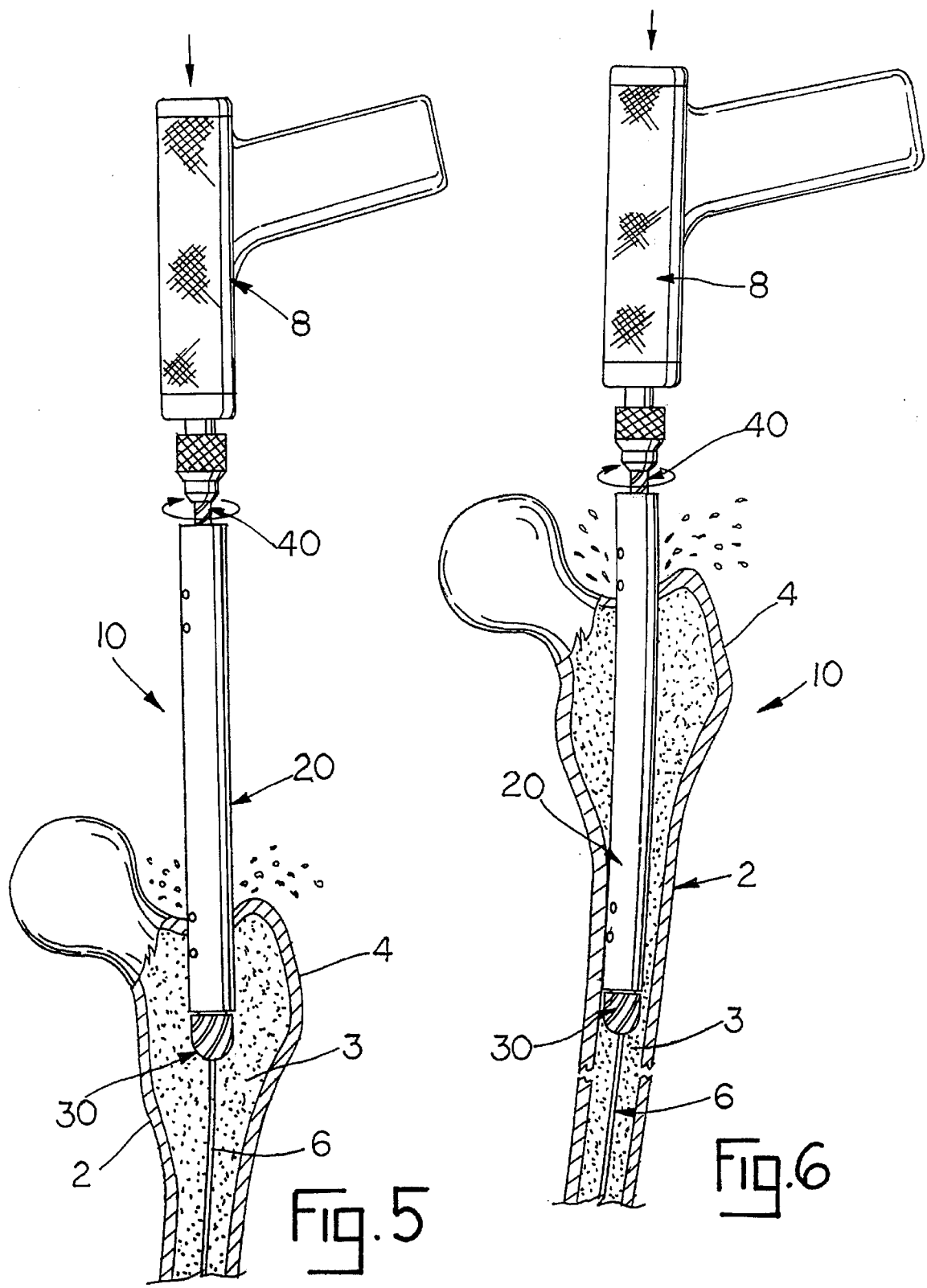
FIG. 5 is a partial sectional view of part of a fractured femur showing the self-reaming IM nail of this invention connected to a rotational driver.
FIGS. 6 is a partial sectional view of part of a fractured femur showing the rotational driver turning the reaming head of the self-reaming IM nail to prepare the medullary canal of the femur as the IM nail is inserted into the prepared canal.
Figure 7:
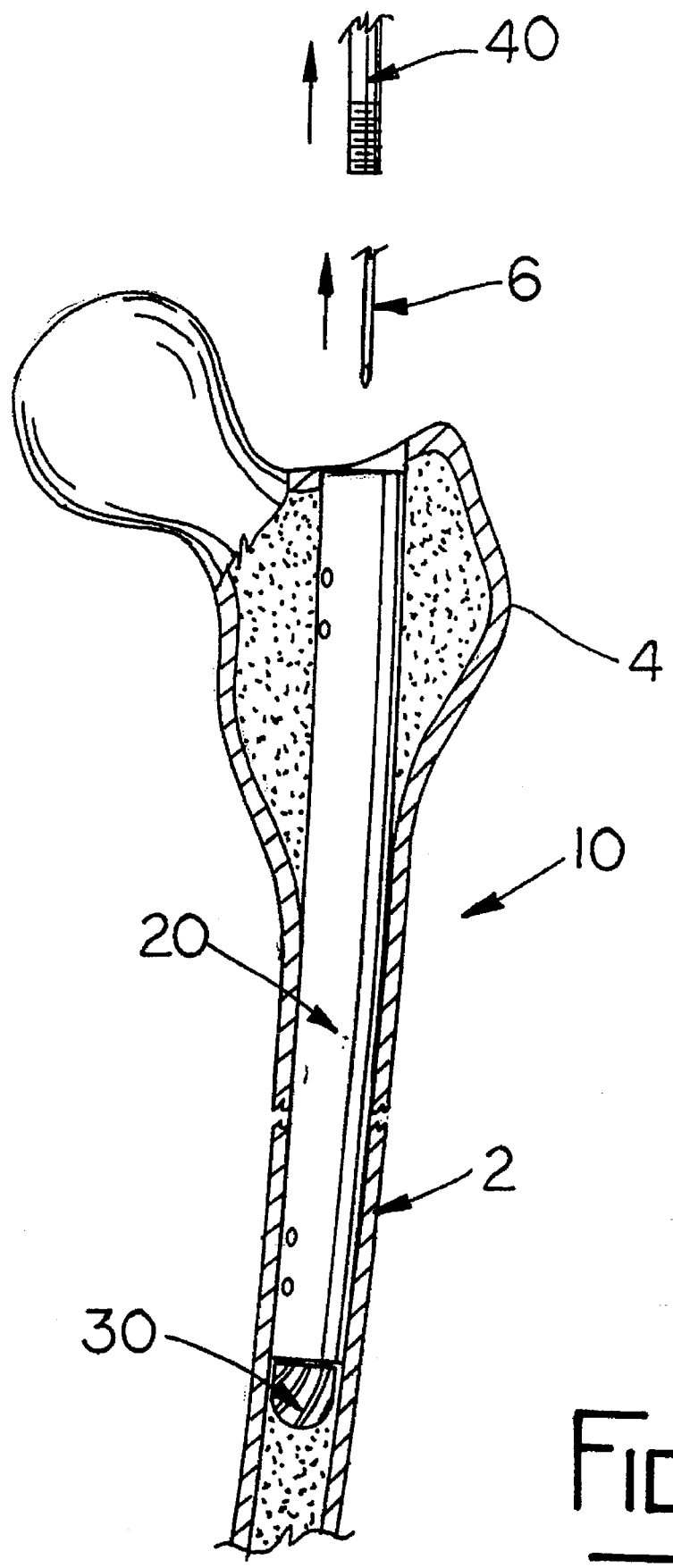
FIG. 7 is a partial sectional view of part of a fractured femur showing the IM nail positioned within the intramedullary channel with the drive shaft and guide wire withdrawn.

FIGS. 3–7 illustrate the procedure for inserting nail 10 within the medullary canal 3 of a fractured long bone, such as a femur 2. For convenience, drive shaft 40 is connected to nail 10 prior to use. FIG. 3 shows guide wire 6 is extending through medullary canal 3 from the femur 2. Guide wire 6 is inserted through a small pilot hole in the upper portion 4 of femur 2 using conventional surgical techniques that are well known in the medical arts. Once the guide wire is properly inserted in the medullary canal, nail 10 and its attached drive shaft 40 are passed over guide wire 6, as shown in FIG. 4. Next, rotational driver 8 is connected to drive end 44 of drive shaft 40. With rotational driver 8 connected to drive shaft 40, nail 10 is positioned against bone 2 and aligned with medullary canal 3. As shown in FIGS. 5–6, rotational driver 8 turns drive shaft 40 within nail bore 21, thus turning reaming head 30 relative to nail body 20 to clear a passage for nail 10 as it moves down guide wire 6. The rotation of reaming head 30 also draws nail body 20 into medullary canal 3. Once nail 10 is inserted to the proper depth within fractured bone 2, rotational driver 8 is disconnected from drive shaft 40. Next, drive shaft 40 is disconnected from reaming head 30 and withdrawn from nail body 20 along with guide wire 6, as shown in FIG. 7. Finally, locking screws (not shown) can be inserted through bores 23, 25 to secure nail 10 within femur 2 as desired.

It is understood that the above description does not limit the invention to the details given, but may be modified within the scope of the following claims.

I claim:

1. A surgical nail adapted for use with a rotational driver for fixation within a bone comprising:

a cannulated nail body having a proximal end and a distal end and a longitudinal bore extending therethrough, a reaming head rotatably connected relative to said body distal end and including blade means for cutting a portion of said bone to prepare said bone for receiving said nail when said reaming head is rotated, a drive shaft within said body bore for connecting said reaming head to said rotational driver to transfer rotational movement from said driver to said reaming head.

2. The nail of claim 1 wherein said body distal end includes an annular end flange, said reaming head includes a neck part journaled within said end flange for rotational movement about the longitudinal axis of said reaming head and for rotational movement of said head relative to said body distal end.

3. The nail of claim 1 wherein said drive shaft has a longitudinal bore and said reaming head has a longitudinal bore, said reaming head bore and said drive shaft bore longitudinally communicating to define a passage for receiving a guide wire when said drive shaft is connected to said reaming head.

4. The nail of claim 1 wherein said nail is an intramedullary nail adapted for use within a long bone having a medullary canal.

5. A surgical nail adapted for use with a rotational driver for fixation within a bone comprising:

a cannulated nail body having a proximal end and a distal end and a longitudinal bore extending therethrough, a reaming head rotatably connected to said body distal end and including blade means for cutting a portion of said bone to prepare said bone for receiving said nail when said reaming head is rotated, a drive shaft within said body bore for connecting said reaming head to said rotational driver to transfer rotational movement from said driver to said reaming head, and wherein said drive shaft is a detachable drive shaft which includes a distal end having means for connecting said drive shaft to said reaming head and a proximal end having means for connecting said drive shaft to said driver.

6. The nail of claim 5 wherein said reaming head includes a female part, and said distal connecting means includes a male part for connective engagement within said reaming head female part.

7. The nail of claim 5 wherein the means for connecting said drive shaft to said reaming head is a threaded interconnection.

8. A surgical nail adapted for use with a rotatable driver for fixation within a bone comprising:

a nail body having a proximal end and a distal end, a separate reaming head interconnected to said body distal end and, said head including a cutting means for cutting a portion of said bone to prepare said bone for receiving said nail when said reaming head is rotated, a drive means for interconnecting with said driver to rotatably drive said nail into the bone, and wherein said head is rotatably interconnected relative to said body distal end.

9. The nail of claim 8 wherein said nail body has a longitudinal bore extending therethrough, and wherein the drive means includes a drive shaft within said body bore for connecting said reaming head to said driver to transfer rotational movement from said driver to said reaming head.

10. A method for inserting a self-reaming intramedullary nail into a fractured bone having a medullary canal, said nail including a cannulated nail body having a proximal end and a distal end and a longitudinal bore extending therethrough, a reaming head rotatably connected to said body distal end and including blade means for cutting a portion of said bone when said reaming head is rotated to prepare said canal for receiving said nail, and a detachable drive shaft insertable into said body bore for connecting said reaming head to a rotational driver to transfer rotational movement to said reaming head from said driver, said shaft has a longitudinal bore and said reaming head has a longitudinal bore, said reaming head bore and said shaft means bore longitudinally communicating to define a passage for receiving a guide wire when said shaft means is connected to said reaming head, said method comprising the steps of:
a) exposing said fractured bone;
b) inserting a guide wire into said canal;
c) inserting one end of said drive shaft into said body bore and connecting said drive shaft to said reaming head;
d) passing said nail and connected drive shaft over said guide wire;
e) connecting the other end of said drive shaft to a rotational driver;
f) activating said driver to rotate said reaming head and driving said nail into said canal to a position across said fracture as said rotating reaming head prepares said canal;
g) disconnecting said driver from said drive shaft and said drive shaft from said reaming head; and
h) withdrawing said drive shaft and said guide wire from said nail body.

* * * * *